Figure 1:
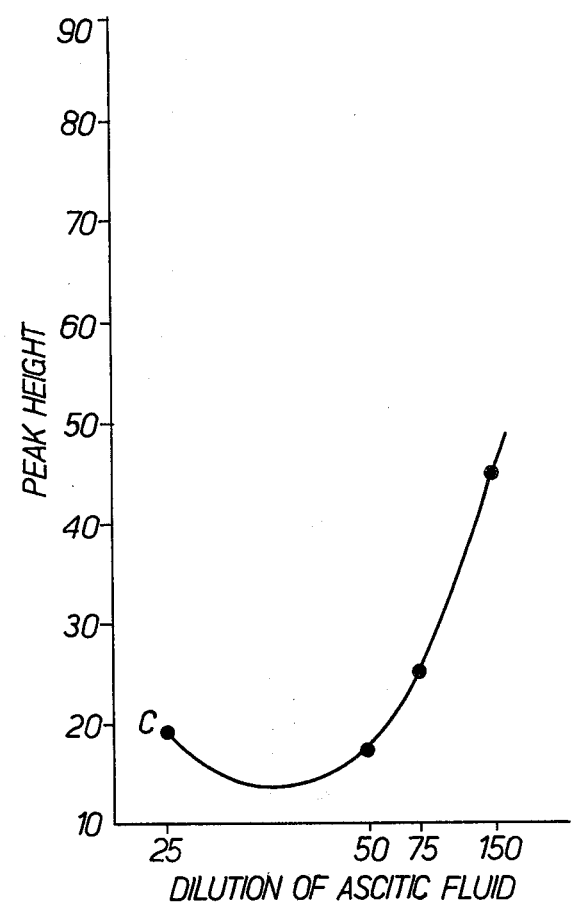

United States Patent [19]

Masson et al.

[11] 4,307,190

[45] Dec. 22, 1981

[54] IMMUNOASSAY USING ASCITIC FLUID

[75] Inventors: Pierre L. Masson, Brussels; Cesar L. Cambiaso, Kraainem, both of Belgium

[73] Assignee: Technicon Instruments Corporation, Tarrytown, N.Y.

[21] Appl. No.: 88,239

[22] Filed: Oct. 25, 1979

[30] Foreign Application Priority Data

Oct. 30, 1978 [GB] United Kingdom ............... 42432/78

[51] Int. Cl.$^3$ .................................. G01N 33/54
[52] U.S. Cl. ................................. 435/7; 424/1; 424/8; 424/12; 23/230 B
[58] Field of Search ............... 435/7, 188, 810; 424/1, 424/8, 12, 1.5; 23/230 B; 424/1, 8, 12, 1.5; 23/230 B

[56] References Cited

U.S. PATENT DOCUMENTS

| | | | |
|---|---|---|---|
| 4,062,935 | 12/1977 | Masson et al. | 435/7 |
| 4,092,114 | 5/1978 | Buck | 424/12 |
| 4,134,792 | 1/1979 | Boguslaski et al. | 435/7 |
| 4,138,213 | 2/1979 | Masson et al. | 435/7 |
| 4,162,895 | 7/1979 | Cambraso et al. | 424/12 |

FOREIGN PATENT DOCUMENTS 2832853  2/1979 Fed. Rep. of Germany .......... 435/7

OTHER PUBLICATIONS

Van de Winkel et al., "Interference of Serum Glycoproteins in Radio Immunoassay of Rat Alfa-Fetoprotein", *Chemical Abstracts*, vol. 87, No. 19 (1977), p. 261, Abs. No. 148242x.

*Primary Examiner*—Thomas G. Wiseman
*Attorney, Agent, or Firm*—S. P. Tedesco

[57] ABSTRACT

A liquid, particularly but not exclusively a liquid of human origin such as blood serum or urine, is immunoassayed for antibodies, antigens or antibody:antigen complexes, using as a reagent in the analysis an active fraction from mouse ascitic fluid. This active fraction is a euglobulin and has the ability, like human C1q, to combine with antibody:antigen complexes but not with free antibody or antigen. Unlike human C1q, however, it remains active at high pH's and its activity is not destroyed by 0.1 M putrescine or 0.1 M hydrazine, so analyses on human body fluids can be carried out at high pH's or in the presence of putrescine and hydrazine, without interference from endogenous human C1q. The active fraction is a very broadly applicable reagent in immunoassays and particularly useful in techniques involving agglutination of latex particles.

22 Claims, 3 Drawing Figures

IMMUNOASSAY USING ASCITIC FLUID

This invention relates to the analysis of liquids, particularly but not exclusively biological fluids such as serum or urine, for the presence therein of antigens, antibodies and antibody:antigen complexes. In this specification, the symbols "Ag", "Ab" and "Ab:Ag" are used respectively for antigen(s) (by which term we include haptens and other substances which can be bound by antibodies or similar binding proteins), antibody(ies) (including similar binding proteins) and antibody:antigen complex(es).

As is well known, it is important to be able to analyse liquids, particularly biological liquids, for Ab, Ag or Ab:Ag therein. For example, many diseases are characterised by the presence in the circulation of Ab:Ag, and hence their detection and characterisation can provide information of value in the diagnosis of disease. There are a number of techniques known for detecting and quantifying Ag, Ab and Ab:Ag and particulaly for determining the nature and amount of Ag present. These quantification techniques are called "immunoassay" procedures.

In Journal of Immunology, Vol. 84 (1959), page 514, Lieberman et al describe the properties of ascitic fluid generated in the peritonea of mice by injecting antigenic materials derived from various sources. They found that high yields of ascitic fluid could be obtained, for example, from 12-15 ml. per mouse and that the fluid contained various protective and agglutinating antibodies, viable leukocytes and $\gamma$-globulin. The agglutinating antibodies were formed by injecting the mice with various bacteria, the antibodies so formed in the ascitic fluid being capable of agglutinating the particular bacterial antigen giving rise to their formation. We have now made the surprising discovery that acsitic fluid from mice is a very useful reagent in immunoassays, since it possesses the property of combining with Ab:Ag but not with free Ab or Ag. Further, it causes the agglutination of various immunoglobulins when heat aggregated, latex bound or modified in a similar way, although it does not react with polymerised IgG3. These properties are due to the presence in the ascitic fluid of what we term "an active fraction" which is not the antibodies, leukocytes or $\gamma$-globulin previously described.

According to the invention, there is provided a method of analysing a liquid sample for Ab, Ag or Ab:Ag therein, which includes the step of adding to the sample, before or after adding other reagents, the active fraction of ascitic fluid from mice to bind with Ab:Ag present in, or generated in, the sample.

The active fraction of the ascitic fluid which is used in the present invention is euglobulin. In some of its properties, it closely resembles human C1q. For example, it combines with Ab:Ag but not with free Ab or Ag; it has a sedimentation constant of 10S; it selectively binds with IgG and IgM but not IgA; it agglutinates latex particles coated with IgG or IgM; and it attaches to the same portion of the Fc chain of IgG as does human C1Q. In other respects, however, it has quite different properties from human C1q. For example, it remains active at high pH's, e.g. above 8 and, particularly, above 9.2 (at which pH human C1q is inactive); its activity is not destroyed by 0.1 M putrescine or by 0.1 M hydrazine. Unlike C1q, the active fraction of ascitic fluid separates in electrophoresis into two regions, $\alpha$ and $\beta_2$, with a respective pI of 5.6 and 6.5.

The active fraction of ascitic fluid can be obtained by separation techniques commonly used in the art, for example in a manner similar to that in which human C1q is obtained from human serum. Thus, for example, if mouse ascitic fluid is passed through a chromatographic column of aminated agarose having human IgG coupled thereto (by glutaraldehyde), the active fraction of the ascitic fluid will be absorbed. The fraction can then be eluted using 1 M sodium chloride solution. The eluant can be dialysed (to separate the sodium chloride) and finally the active fraction taken up in GBS (0.1 M glycine—HCl buffer, pH 9.2).

Insofar as the active fraction of mouse ascitic fluid resembles human C1q, it can be used in analyses in the same way as human C1q. The use of human C1q in assays is described in our British patent specification no. 1508133 to which reference should be made for further details.

An important advantage of using the active fraction of mouse ascitic fluid in analyses, instead of human C1q, is that whole mouse ascitic fluid can be used: it is not essential, or even usually necessary, to separate out the active fraction. By contrast, in most analyses where human C1q is used as a reagent, it is not possible to use whole human serum: the C1q must be separated out. The avoidance of such a separation step is highly advantageous. Furthermore, mouse ascitic fluid is far more readily available than is separated human C1q, and is therefore a more economic reagent to use. A further advantage is that the reaction of ascitic fluid may be carried out at a pH of 9.2 where human C1q cannot interfere. A still further advantage of ascitic fluid as compared to human C1q is the fact that ascitic fluid does not react with DNA, endotoxin or heparin, which are all potential interferents in human plasma.

The active fraction of mouse ascitic fluid resembles in many of its properties the active fraction of mouse serum which is described for use in immunoassays in our U.S. Pat. No. 4,162,895. The active fraction of ascitic fluid is not identical to that of mouse serum: for example in electrophoresis two factors in the ascitic fluid fraction have different concentrations from those in mouse serum. However, the active fraction of ascitic fluid can be used in immunoassays in a similar manner to the active fraction of mouse serum and reference should be made in this connection to our U.S. Pat. No. 4,162,895. A particular and substantial advantage of the use of ascitic fluid instead of mouse serum lies in the fact that ascitic fluid is much more readily available. Thus, only about 1 ml of mouse serum can be obtained at a time from a mouse, whereas from 15 to 20 ml of ascitic fluid can be obtained and, surprisingly, the potency of the ascitic fluid (so far as the active fraction is concerned) is closely similar to that of mouse serum.

Among the preferred methods of analysis of the present invention are the following:

(1) A method of assaying an Ab or Ag in a liquid, which comprises
 (a) adding to the liquid an Ag or Ab which is specific to the Ab or Ag, respectively, under assay in the liquid to form an Ab:Ag therewith;
 (b) adding to the mixture from step (a) a known amount of the Ab or Ag to be determined, which amount carries an identifying label;
 (c) adding to the mixture formed in step (b) the said active fraction in an amount at least sufficient to bind with all the Ab:Ag in the mixture; and (d) measuring the amount of labelled Ab or Ag remaining free in the mixture or bound to the said active fraction.

The identifying label may, for example, be an enzyme or co-enzyme such that the activity of the enzyme or co-enzyme is inhibited upon binding of the Ab:Ag or labelled Ab:Ag to the said active fraction, and the amount of free labelled Ab or Ag is determined by measuring the enzyme or co-enzyme activity of the mixture without first removing the Ab:Ag bound to the said active fraction. Suitable such enzymes include catalase and amylase. Alternatively, in the above method (1), the Ab:Ag bound to the said active fraction is removed from the mixture, and the amount of labelled Ag or Ag remaining in the mixture is then measured.

(2) A method of determining the presence in, or absence from, a liquid of an Ab:Ag, which comprises adding to the liquid the said active fraction and a material which is caused to agglutinate on contact with any of the said active fraction not bound to Ab:Ag, and detecting whether or not agglutination of the material occurs. Preferably, the material comprises inert carrier particles such as latex, having a coating of an immunoglobulin (IgG or IgM).

(3) A method of detecting the presence of a particular Ab or Ag in a liquid, which comprises adding to the liquid an Ag or Ab which is specific to the particular Ab or Ag whose presence is to be determined, to form Ab:Ag with any of said particular Ab or Ag present; and determining the presence or absence of such Ab:Ag by the method (2) above.

(4) A method of analysing a liquid for Ab:Ag complexes therein, which comprises adding to the liquid a known amount of inert carrier particles coated with IgG or IgM, the particles being agglutinatable on contact with the Ab:Ag complex and on contact with the said active fraction; and adding also to the liquid a quantity of the said active fraction; incubating the mixture so formed; counting the number of unagglutinated particles; and calculating thereby the amount of complex in the liquid. The Ab:Ag in the liquid may have been formed by adding to a liquid containing an Ab or Ag to be assayed, a respective Ag or Ab to form a liquid containing the Ab:Ag, the amount of Ab or Ag under assay being derived from the calculated amount of complex.

(5) A method of analysing a liquid for Ag therein which comprises adding to the liquid a known amount of inert carrier particles coated with Ab to said Ag, the particles being agglutinatable on contact with the Ag and on contact with said active fraction, and adding also to the liquid a quantity of said active fraction; incubating the mixture so formed; counting the number of unagglutinated particles; and calculating thereby the amount of Ag in the sample.

(6) A method of analysing a liquid for Ab therein which comprises adding to the liquid a known amount of inert carrier particles coated with Ag to said Ab, the particles being agglutinatable on contact with the Ag and on contact with said active fraction, and adding also to the liquid a quantity of said active fraction; incubating the mixture so formed; counting the number of unagglutinated particles; and calculating thereby the amount of Ab in the sample.

In both methods (5) and (6) the inert carrier particles are preferably latex particles, whose size is preferably about 0.8 to 1.1 microns.

In the analysis of human serum samples using human C1q, account has to be taken of the fact that the serum itself will contain human complement C1. To avoid interference from the resulting C1q in the analysis of the serum using human C1q as an added reagent, the serum must first be treated to inactivate the native C1q. One technique for this is to heat the serum to about 56° C. and keep it at that temperature for about 30 minutes. However, whilst this treatment inactivates the native C1q in the serum, it also has other effects on the serum which can render the subsequent analysis less accurate.

By using mouse ascitic fluid (or the separated active fraction thereof) as a reagent according to the present invention, the necessity for this heating step when assaying human sera may be avoided by, for example, conducting the analysis at a high pH, e.g. 9.2. At high pH's, any human C1q in the serum under test is inactive, whereas the mouse ascitic fluid remains active. Alternatively, the analysis could be effected in the presence of 0.1 M hydrazine or 0.1 M putrescine, under which conditions human C1q is inactive but mouse serum is not. These properties of mouse ascitic fluid thus enable the avoidance of interference from native C1q. Thus, mouse ascitic fluid is capable of agglutinating human IgG-coated particles at a pH and ionic strength high enough to remove interference with latex particle agglutination by complement from the patient's serum.

It will be appreciated that this is a highly advantageous feature of using mouse ascitic fluid (or its active fraction) in the analysis of human sera.

The methods of the invention may advantageously be effected by continuous flow techniques, which are known in the art. In continuous flow analyses, mouse ascitic fluid can be more conveniently used as a reagent than human C1q since the manifold and incubation system for human rheumatoid factor is suitable also for use with mouse ascitic fluid but not with human C1q.

We prefer to obtain the ascitic fluid by weekly intraperitoneal injections of complete Freund's adjuvant as described by Tung et al (Journal of Immunology, Vol. 116 (1976), p. 676). With this technique, it is possible to collect repeatedly from 10 to 20 ml. of fluid from one mouse every 3 to 7 days.

EXAMPLE 1

Mouse ascitic fluid will cause the agglutination of IgG-coated latex particles, and also of heat-aggregated IgG, the active fraction of the ascitic fluid reacting preferentially with heat-aggregated IgG.

Thus, if a quantity of mouse ascitic fluid is mixed with IgG-coated latex (latex-IgG) particles, aggregation of the particles will occur. If heat-aggregated IgG is now added, the active fraction from the ascitic fluid will be taken up in agglutinating the heat-aggregated IgG until, eventually, there is no remaining aggregation of the latex. The activity of the ascitic fluid can be expressed in terms of the amount of heat-aggregated IgG necessary to prevent any aggregation of the latex. Similarly, the activity of human serum can be expressed in terms of the amount of heat-aggregated IgG that would have been necessary to prevent to the same extent the agglutination of latex IgG. By making tests on sera from 50 healthy blood donors, this activity has been found to be at most 30 $\mu$g/ml of equivalents of heat-aggregated IgG (EHAIgG).

We have also measured the activity of human sera from patients with multiple sclerosis (75 patients) and from patients with thyroid disorders (58 patients).

Among the patients with multiple sclerosis, 30% had sera activities above 27 μg/ml (EHAIgG) and among the patients with thyroid disorders, 65.5% had sera activities above 27 μg/ml (EHAIgG). It will be appreciated that the higher activity indicates the presence in the sera of immune complexes (these being absent or present only in low levels in healthy patients).

Ascitic fluid has a greater avidity for some immune complexes than for others. RF likewise has a varying avidity for immune complexes. We recommend, therefore, that in tests on human sera for the presence of immune complexes, both mouse ascitic fluid and RF tests be run in parallel. For information concerning the use of RF, reference should be made to our British application Ser. No. 21619/75.

EXAMPLE 2

(1) Preparation of whole mouse ascitic fluid

Whole ascitic fluid was obtained from NMR1 mice by the method described above. It was diluted in GBS (0.1 M glycine-HCl buffer, pH 9.2, containing 0.17 M NaCl). The dilution ranged from 1/50 to 1/80.

(2) Preparation of patients' sera before analysis

A volume of serum of 50 μl was added to 170 μl of GBS containing 50 mM EDTA (pH 9.2) and then reduced using 15 μl dithiothreitol (5 μg/ml) for 15 minutes at 37° C. The sample is then reoxidized by 15 μl of 0.2% $H_2O_2$ to destroy the dithiothreitol. This reduction of the serum sample aimed to eliminate any agglutinating factor which could interfere with the inhibition process. The reoxidation is necessary to inactivate the residual dithiothreitol which could destroy the agglutinating factor of the mouse ascitic fluid. It is to be noted that whilst this treatment will to a limited extent inactivate endogenous C1q in the sera, its main purpose is to inactivate other agglutinating factors such as RF. Full inactivation of C1q is achieved by conducting the analyses at a pH of 9.2. This pretreatment dilutes the serum 5-fold.

(3) Preparation of latex

Polystyrene particles (0.794 μ) from Dow Chemical Company (Indianapolis, Ind.) are coated with human IgG as follows. To 400 μl of 5-fold diluted GBS, are added 25 μl of a 1% (w/v) solution of IgG, 150 μl of 1% (w/v) solution of human serum albumin (Behringwerke, Marburg, West Germany), and then 50 μl of the 10% (w/v) latex suspension. After vortexing for a few seconds and incubating at room temperature for 45 minutes, the suspensions are centrifuged at 10,000 rev/min for 5 minutes, the particles are washed once with 1 ml diluted GBS, and finally resuspended in 10 ml. GBS containing 1% (w/v) bovine serum albumin.

(4) Automated Analysis

The same volumes (50 μl) of serum sample, diluted mouse ascitic fluid and latex suspension, as described above, are aspirated together into the manifold. The incubation time is 10 minutes. After incubation, the mixture is diluted 2000 times automatically with GBS containing 0.1% Tween 20, and the non-agglutinated latex particles were then counted in a Technicon optical cell counter (Autocounter) with a lower and upper threshold. The run requires a 2000-fold dilution of the latex suspension to restrict the count to a maximum of 4000 particles/sec.

(5) Results

Serial two-fold dilutions of mouse ascitic fluid give the agglutination curve of FIG. 1. The ordinates represent the height of the peaks on the recorder. The height is directly proportional to the number of free (non-agglutinated) particles. The latex contained about 16000 molecules IgG per particle.

Figure 2:
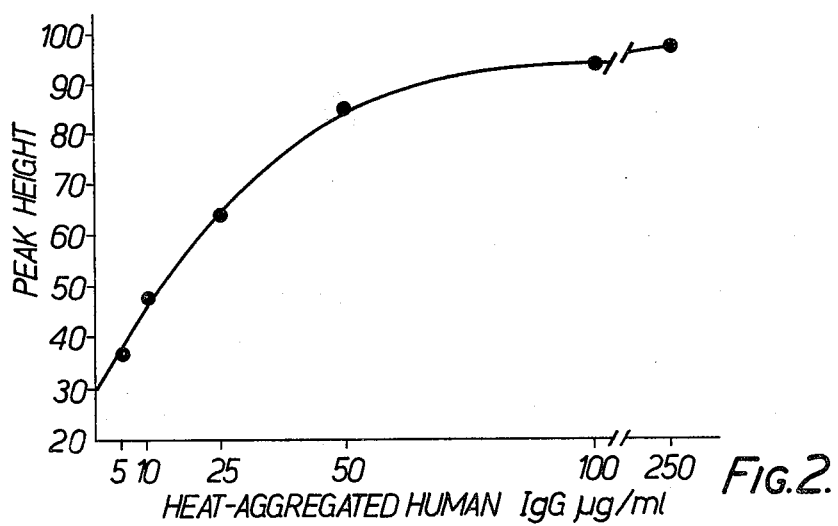

Standard curve (FIG. 2) is determined with a range of concentration, of heat-aggregated IgG in GBS. The results are expressed in μg/ml of equivalents of heat-aggregated human IgG. The latter are prepared by DEAE-cellulose chromatography from a pool of human sera and aggregated by heating at 63° C. for 30 minutes.

Figure 3:
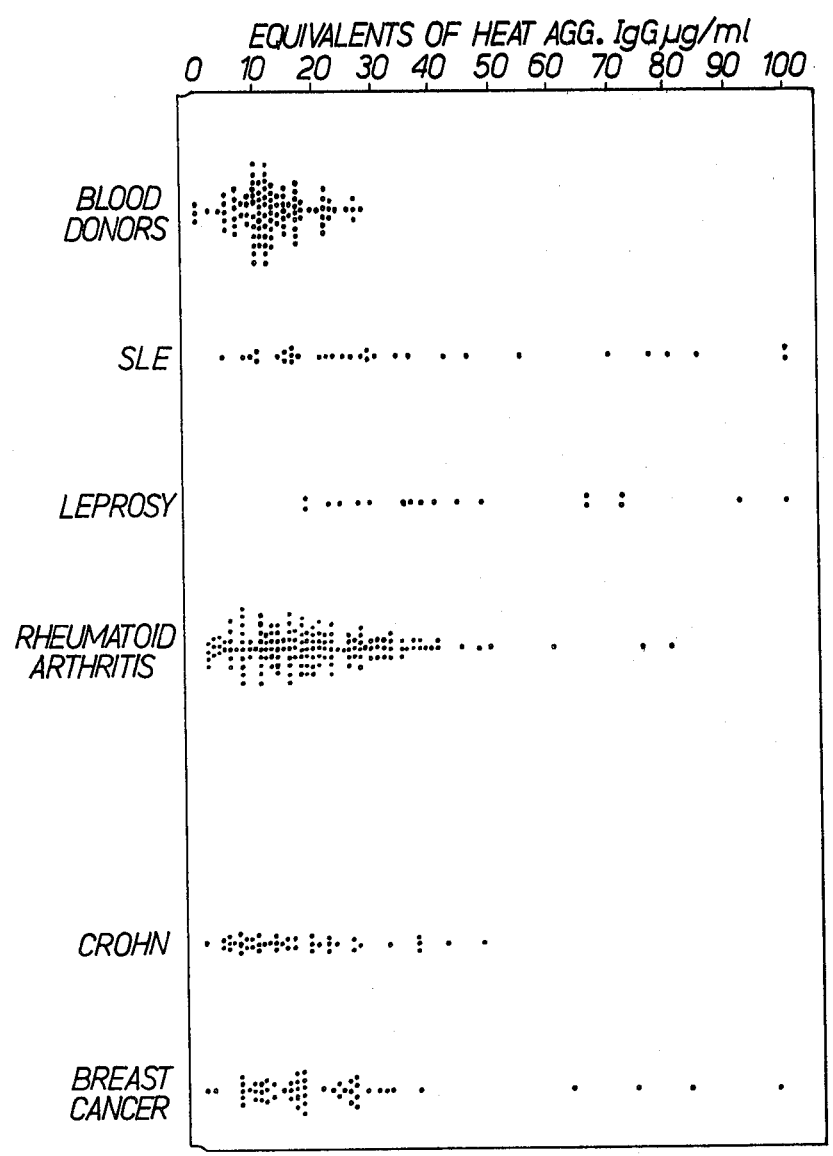

FIG. 3 represents the results of the inhibition of mouse serum by sera from healthy blood donors, patients with systemic lupus erythematosus (SLE), leprosy, rheumatoid arthritis, Crohn's disease and breast cancer. The upper limit for the normal values is about 30 μg/ml of equivalents of heat-aggregated IgG.

The method of the invention is particularly useful in the in vitro assay of liquids of human origin, for example in the diagnosis of disease. It also is useful in many industrial applications, such as blood banks, for detecting abnormalities in blood.

We claim:

1. In a method for assaying an Ab or Ag in a liquid comprising the steps of:
    (a) adding to the liquid an euglobulin and an Ag or Ab which is specific to the Ab or Ag, respectively, under assay in the liquid to form a mixture under conditions suitable for forming an Ab:Ag complex;
    (b) adding to the mixture formed in step (a) a known amount of labelled Ab or Ag which Ab or Ag corresponds to the Ab or Ag assayed;
    (c) measuring the amount of labelled Ab or Ag remaining free in the mixture or bound to the euglobulin, wherein the improvement comprises using euglobulin capable of binding Ag:Ab complexes at a pH above 8 and derived from the active fraction of mouse ascitic fluid.

2. The method of claim 1 wherein the euglobulin is added in the form of whole ascitic fluid.

3. The method according to claim 1 wherein the liquid is a biological liquid of human origin.

4. In a method for assaying an Ab in a liquid comprising the steps of:
    (a) adding to the liquid a known amount of inert carrier particles coated with Ag to the Ab, the particles being agglutinable on contact with both the Ab and euglobulin, and euglobulin to form a mixture;
    (b) incubating the mixture formed in step (a);
    (c) counting the number of unagglutinated particles; and
    (d) calculating thereby the amount of Ab in the sample, the improvement comprises using in step (a) euglobulin capable of binding Ab:Ag complexes at a pH above 8 and derived from the active fraction of mouse ascitic fluid.

5. The method of claim 4 wherein the euglobulin binds with Ab:Ag in the presence of 0.1 M putrescine or 0.1 M hydrazine.

6. The method of claim 4 which is effected on a continuous flow basis.

7. The method of claim 4 comprising adding in step (a) a material which is caused to agglutinate on contact with any of the euglobulin not bound to Ab:Ag; and detecting after step (c) whether or not the agglutination occurs.

8. The method of claim 7 wherein the material comprises inert carrier particles coated with a substance selected from the group consisting of IgG and IgM.

9. The method of claim 8 wherein the particles are latex particles.

10. The method of claim 9 wherein the size of the particles is from about 0.8 microns to about 1.1 microns.

11. In a method for analyzing a liquid for Ab:Ag complexes therein comprising the steps of:
 (a) adding to the liquid a known amount of inert carrier particles coated with a substance selected from the group consisting of IgG and IgM, the particles being agglutinable on contact with both Ab:Ag complex and euglobulin, and euglobulin to form a mixture;
 (b) incubating the mixture formed in step (a);
 (c) counting the number of unagglutinated particles and calculating thereby the amount of complex in the liquid;
 the improvement comprising using in step (a) euglobulin capable of binding Ab:Ag complexes at a pH above 8 and derived from the active fraction of mouse ascitic fluid.

12. The method of claim 11 wherein the inert carrier particles are latex particles.

13. The method of claim 12 wherein the size of the particles is about 0.8 microns to about 1.1 microns.

14. The method of claim 11 wherein the Ab:Ag in the liquid in step (a) has been formed by adding to a liquid containing an Ab or Ag to be assayed a respective Ag or Ab to form a liquid containing said Ab:Ag, and wherein the amount of the Ab or Ag under assay is ascertained from the amount of complex calculated in step (c).

15. In a method for assaying an Ag in a liquid comprising the steps of:
 (a) adding to the liquid a known amount of inert carrier particles coated with Ab to the Ag assayed, the particles being agglutinable on contact with both the Ag and euglobulin, and euglobulin to form a mixture;
 (b) incubating the mixture formed in step (a);
 (c) counting the number of unagglutinated particles; and
 (d) calculating thereby the amount of Ag in the sample; the improvement comprising using in step (a) euglobulin capable of binding Ab:Ag complexes at a pH above 8 and derived from the active fraction of mouse ascitic fluid.

16. The method of claim 15 wherein the inert carrier particles are latex particles.

17. The method of claim 15 wherein the pH is at least 9.2.

18. In a method for assaying Ab or Ag in a liquid comprising the steps of:
 (a) adding to the liquid an Ag or Ab which is specific to the Ab or Ag, respectively, under assay in the liquid to form a mixture under conditions suitable for forming an Ab:Ag complex;
 (b) adding to the mixture from step (a) a known amount of labelled Ab or Ag which Ab or Ag corresponds to the Ab or Ag to be determined and a euglobulin;
 (c) measuring the amount of labelled Ab or Ag remaining free in the mixture or bound to the euglobulin, wherein the improvement comprises using in step (b) a euglobulin capable of binding Ab:Ag complexes at a pH above 8 and derived from the active fraction of mouse ascitic fluid.

19. The method of claim 18 wherein the euglobulin is added in the form of whole mouse ascitic fluid.

20. The method of claim 18 wherein the liquid to be assayed is a biological fluid of human origin.

21. The method of claim 18 wherein the identifying label is an enzyme or co-enzyme which is inhibited upon binding of the Ab:Ag or labelled Ab:Ag to the euglobulin, and the amount of free labelled Ab or Ag is determined by directly measuring the enzyme or co-enzyme activity of the mixture.

22. The method of claim 21 wherein the label is selected from the group consisting of catalase and amylase.

* * * * *